(12) United States Patent
Rosenbaum

(10) Patent No.: US 6,750,235 B1
(45) Date of Patent: Jun. 15, 2004

(54) PRAMIPEXOLE AS A TREATMENT FOR COCAINE CRAVING

(75) Inventor: Jerrold Rosenbaum, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/088,628

(22) PCT Filed: Sep. 28, 2000

(86) PCT No.: PCT/US00/26634

§ 371 (c)(1),
(2), (4) Date: Jun. 12, 2002

(87) PCT Pub. No.: WO01/22820

PCT Pub. Date: Apr. 5, 2001

Related U.S. Application Data

(60) Provisional application No. 60/156,860, filed on Sep. 30, 1999.

(51) Int. Cl.7 ........................ A61K 31/425; A61K 31/53
(52) U.S. Cl. ........................ 514/367; 514/242; 514/241
(58) Field of Search ................................. 514/367, 241, 514/242

(56) References Cited

U.S. PATENT DOCUMENTS 5,650,420 A     7/1997  Hall et al. .................. 514/367

OTHER PUBLICATIONS

Cain et al., "D3 receptor test in vitro predicts decreased cocaine self–administration in rats" *NeuroReport* 8:2373–2377, 1997.*

Abstract of EP 417,637 A2, Kutter et al., Mar. 20, 1991.*

Bayuk et al., "The effects of pramipexole on cue induced craving" *38th Annual Meeting of American College of Neuropsychopharmacology*, Abstract 51 (Dec. 1999).

Buydens–Branchey et al. "Buspirone attenuates withdrawal symptoms in cocaine addicts" *38th Annual Meeting of American College of Neuropsychopharmacology*, Abstract 52 (Dec. 1999).

Caine et al., "$D_3$receptor test in vitro predicts decreased cocaine self–administration in rats" *NeuroReport* 8:2373–2377 (1997).

Eiler et al., "Double–blind comparison of bromocriptine and placebo in cocaine withdrawal" *Am. J. Drug Alcohol Abuse* 21:65–79 (1995).

Filip et al., "The role of dopamine receptor subtypes in the discriminative stimulus effects of amphetamine and cocaine in rats" *Pol. J. Pharamcol.* 49:21–30 (1997).

* cited by examiner

*Primary Examiner*—Dwayne C. Jones
(74) *Attorney, Agent, or Firm*—Clark & Elbing LLP

(57) ABSTRACT

Disclosed herein are methods foe reducing stimulant dependency or craving, involving administration of a therapeutically-effective amount of a dopamine agonist, such as pramipexole.

9 Claims, 1 Drawing Sheet

PRAMIPEXOLE AS A TREATMENT FOR COCAINE CRAVING

This application claims the benefit of Provisional Application No. 60/156,860 filed Sep. 30, 1999.

BACKGROUND OF THE INVENTION

This invention relates to methods for the treatment of cocaine craving.

Cocaine is a highly addictive pyschostimulant that causes sensations of euphoria and craving, resulting in physiological as well as psychological damage. Although cocaine use leads to a multitude of physiological complications, its primary target of action is the central nervous system. Cocaine withdrawal following abstinence causes, among other symptoms, an intense craving for the abused drug, which in turn frequently results in the relapse into renewed drug use. Epidemiological studies point to a high incidence of multiple substance abuse among cocaine users, a finding that has significant societal and medical repercussions.

To date, approved pharmacotherapies for cocaine abuse and dependence have proven scarce despite the acute need for such therapies.

SUMMARY OF THE INVENTION

In general, the invention features methods for treating stimulant dependencies, such as cocaine craving, by administering a therapeutically-effective amount of a dopamine agonist, for example, pramipexole.

In one aspect, the invention provides a method of treating a patient (for example, a human) with a stimulant dependency by administering a therapeutically-effective amount of pramipexole to the patient. In preferred embodiments of this aspect, the stimulant dependency is a stimulant craving and the stimulant is cocaine.

In a related aspect, the invention provides a method of treating a human diagnosed with cocaine craving by administering a therapeutically-effective amount of pramipexole to the human.

In preferred embodiments of both of the above aspects of the invention, the method further includes administering a therapeutically-effective amount of an antidepressant or an anticonvulsant, for example, lamotrigine.

By "treating" is meant the medical management of a patient with the intent that a cure, amelioration, or prevention of a dependency or a relapse or associated disease, pathological condition, or disorder will result. This term includes active treatment, that is, treatment directed specifically toward improvement of the dependency or associated cure of a disease, pathological condition, or disorder, and also includes causal treatment, that is, treatment directed toward removal of the cause of the dependency or associated disease, pathological condition, or disorder. In addition, this term includes palliative treatment, that is, treatment designed for the relief of symptoms rather than the curing of the dependency, disease, pathological condition, or disorder; preventive treatment, that is, treatment directed to prevention of the dependency or associated disease, pathological condition, or disorder; and supportive treatment, that is, treatment employed to supplement another specific therapy directed toward the improvement of the dependency or associated disease, pathological condition, or disorder. The term "treating" also includes symptomatic treatment, that is, treatment directed toward constitutional symptoms of the dependency or an associated disease, pathological condition, or disorder.

By "stimulant" is meant any substance that temporarily increases functional activity, and preferably cardiac, respiratory, cerebral, nervous, vascular, motor, or vasomotor functional activity. Preferred stimulants include, without limitation, cocaine, amphetamines, methamphetamine, and methylphenidate.

By "therapeutically-effective amount" is meant an amount of a pramipexole compound sufficient to produce a healing, curative, or ameliorative effect either in the treatment of a stimulant dependency or in the symptoms of a stimulant dependency, for example, cocaine craving.

By "dependency" is meant any form of behavior that indicates an altered or reduced ability to make decisions resulting, at least in part, from the use of stimulants. Representative forms of dependency behavior may take the form of antisocial, inappropriate, or illegal behavior and include those behaviors directed at the desire, planning, acquiring, and use of stimulants. This term also includes the psychic craving for a drug that may or may not be accompanied by a physiological dependency, as well as a state in which there is a compulsion to take a drug, either continuously or periodically, in order to experience its psychic effects or to avoid the discomfort of its absence. Forms of "dependency" include habituation, that is, an emotional or psychological dependence on a compound to obtain relief from tension and emotional discomfort, as well as physical or physiological dependence, that is, use of a compound to prevent withdrawal symptoms.

By "craving" is meant a behavior that reflects a consuming desire, longing, or yearning for a stimulant. This term may refer to aspects of behaviors that are components of a dependency.

The present invention provides a number of advantages. Importantly, it provides one of the first therapeutics for the treatment of stimulant cravings (such as cocaine craving). In addition, the pramipexole utilized herein is non-toxic, is pharmocokinetically understood, and is known to be well tolerated by humans, as is evidenced by its approval for the treatment of Parkinson's Disease.

DETAILED DESCRIPTION OF THE INVENTION

Figure 1:
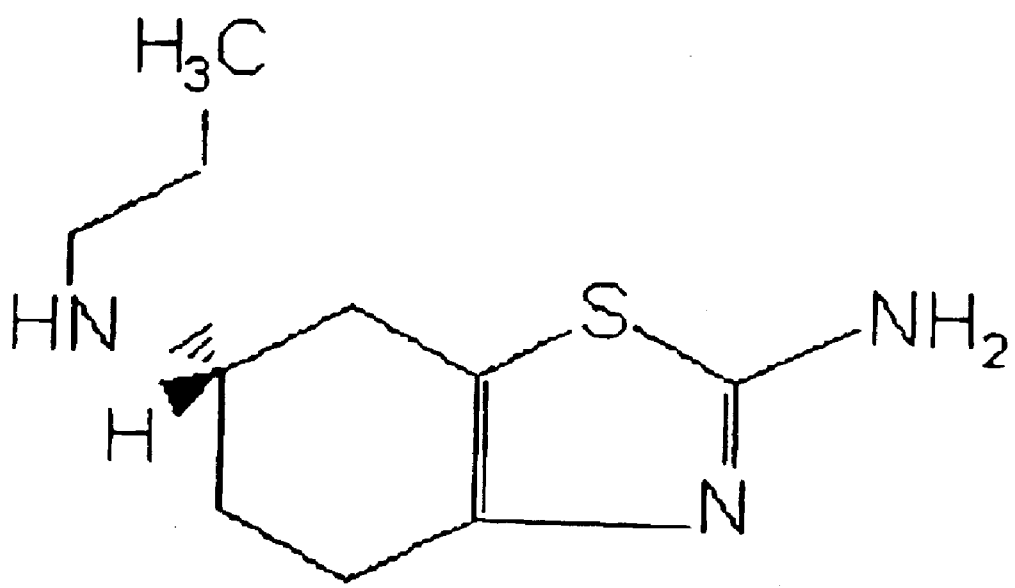
FIG. 1 is a schematic illustration of the molecular structure of pramipexole, marketed as Mirapex in the United States.

The invention described herein features methods involving the administration of pramipexole (or other dopamine-D3/D2 agonists) for the treatment of stimulant dependency, and preferably for the treatment of cocaine craving and its symptoms, as well as cocaine dependency and associated self-destructive behaviors.

Described below is an example of the successful use of pramipexole for the treatment of cocaine craving and related symptoms. This example is provided for the purpose of illustrating the invention, and should not be construed as limiting.

Treatment of Cocaine Craving Using Pramipexole

Mr. A, a 34 year-old single, successful business man, was referred for evaluation of possible bipolar disorder. Currently depressed, he had in the previous year brought financial ruin on himself by a pattern of cocaine freebasing and sexual and other extravagance that absorbed nearly one million dollars.

Along with current major depression, persisting cocaine craving but rare use, and a question of past primary or secondary (to substance abuse) mania, he manifested an extraordinary movement disorder with constant restlessness and thrashing of his legs, leaving the inner aspects of his knees and thighs bruised and discolored with hematomas in various stages of evolution and resolution.

For the restless legs, he bad consulted a neurologist who diagnosed "pre-parkinsonism" presumed secondary to neurological damage from cocaine. The disfiguring movements limited his ability to return to and conduct business.

Previously, he had failed to respond to or tolerate most of the new generation of antidepressants. Treatment was begun with lamotrigine up to 200 mg with modest improvement in mood. Given his severe restless legs syndrome and persisting depression, pramipexole was added, titrated to 1.5 mg a day in divided doses.

In response to this treatment, his leg movements quieted substantially, his mood brightened, and he reported that these were the first days in a year that he awoke without craving cocaine, a benefit sustained for one year on this drug, combined with 75 mg of lamotrigine. During the subsequent year, Mr. A. reported one day of non-compliance when he was out of town without his medication. That night, for the first time, he dreamt about cocaine and the next day experienced a renewed craving on awakening which resolved when treatment was restored.

Although he faces an array of financial and business challenges, his mood following treatment is nearly euthymic, his leg movements at worst resemble mild restlessness, and his cocaine craving remains abolished.

These dramatic results demonstrate that dopamine agonists, like pramipexole, represent treatments for cocaine craving, and may be particularly useful for patients with comorbid refractory depression.

Pramipexole and Other Dopamine Agonists

The synthesis of pramipexole is described in U.S. Pat. No. 4,886,812 and European Patent 186 087. Pramipexole is a non-ergot derivative which may be used at a range of between about 1.5 mg to 6.0 mg per day, and is preferably administered between about 1.5 mg and 4.5 mg per day. Higher dosages may be used with the concomitant risk of potential side effects.

Other formulations for treatment or prevention of stimulant dependency or craving, such as cocaine craving, as described herein, may take the form of a dopamine agonist compound that may be combined with a pharmaceutically-acceptable diluent, carrier, stabilizer, or excipient. Conventional pharmaceutical practice is employed to provide suitable formulations or compositions to administer such compositions to patients. Oral administration is preferred, but any other appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of liquids, tablets or capsules; and for intranasal formulations, in the form of powders, nasal drops, or aerosols.

Methods well known in the art for making formulations are described, for example, in "Remington: The Science and Practice of Pharmacy" (19th ed.) ed. A. R. Gennaro A. R., 1995, Mack Publishing Company, Easton, Pa. Formulations for parenteral administration may, for example, contain excipients, sterile water, saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

In general, a dopamine agonist for use in the methods of the invention is administered at a dosage appropriate to the effect to be achieved and is typically administered in unit dosage form. As noted above, the preferred route of administration for most indications is oral.

An effective quantity of a dopamine agonist-containing compound of the invention is employed to treat the stimulant dependency or craving, for example, cocaine craving as described herein. The exact dosage of the compound may be dependent, for example, upon the age and weight of the recipient, the route of administration, and the severity and nature of the symptoms to be treated. In general, the dosage selected should be sufficient to prevent, ameliorate, or treat the condition, or one or more symptoms thereof, without producing significant toxic or undesirable side effects.

Combination with Other Therapeutics

One particular source of pramipexole is Pharmacia & Upjohn, Inc. which markets Mirapex (Pramipexole Dihydrochloride) tablets which have the molecular structure shown in FIG. 1. Examples of other dopamine agonists include, but are not limited to, amantadine, bromocriptine, cabergoline, lisuride, pergolide, ropinirole, quinpirole, or quinelorane. Pramipexole, or any other dopamine agonist, may be administered as a monotherapy, or in combination with other compounds, for the treatment of multiple substance abuse or other physiological or psychological conditions.

In one particular example, the dopamine agonist (e.g. pramipexole) may be administered in combination with an antidepressant, anticonvulsant, antianxiety, antimanic, antipyschotic, antiobsessional, sedative-hypnotic, or stimulant medication. Examples of these medications include, but are not limited to, the antianxiety medications alprazolam, buspirone hydrochloride, chiordiazepoxide, chlordiazepoxide hydrochloride, clorazepate dipotassium, desipramine hydrochloride, diazepam, halazepam, hydroxyzine hydrochloride, hydroxyzine pamoate, lorazepam, meprobamate, oxazepam, prazepam, prochlorperazine maleate, prochlorperazine, prochlorperazine edisylate, and trimipramine maleate; the anticonvulsants amobarbital, amobarbital sodium, carbamazepine, chlordiazepoxide, chlordiazepoxide hydrochloride, clorazepate dipotassium, diazepam, divalproex sodium, ethosuximide, ethotoin, gabapentin, lamotrigine, magnesium sulfate, mephenytoin, mephobarbital, metbsuximide, paramethadione, pentobarbital sodium, phenacemide, phenobarbital, phenobarbital sodium, phensuximide, phenytoin, phenytoin sodium, primidone, secobarbital sodium, trimethadione, valproic acid, and clonazepam; the antidepressants amitriptyline hydrochloride, amoxapine, bupropion hydrochloride, clomipramine hydrochloride, desipramine hydrochloride, doxepin hydrochloride, fluoxetine, fluvoxamine, imipramine hydrochloride, imipramine pamoate, isocarboxazid, lamotrigine, maprotoline hydrochloride, nortriptyline hydrochloride, paroxetine hydrochloride, phenelzine sulfate, protriptyline hydrochloride, sertraline hydrochloride, tranylcypromine sulfate, trazodone hydrochloride, trimipramine maleate, and venlafaxine hydrochloride; the antimanic medications lithium carbonate and lithium citrate; the antiobsessional medications fluvoxamine, and clomipramine hydrochloride; the antipsychotic medications acetophenazine maleate, chlorpromazine hydrochloride, chlorprothixene, chlorprothixene hydrochloride, clozapine, fluphenazine decanoate, fluphenazine enathrate, fluphenazine hydrochloride, haloperidol decanoate, haloperidol, haloperidol lactate, lithium carbonate, lithium citrate, loxapine hydrochloride, loxapine succinate, mesoridazine besylate, molindone hydrochloride, perphenazine, pimozide, prochlorperazine maleate, prochlorperazine, prochlorperazine edisylate, promazine hydrochloride, risperidone, thioridazine, thioridazine hydrochloride; thiothixene, thiothixene hydrochloride, and trifluoperzine hydrochloride; the sedative-hypnotic medications amobarbital, amobarbital sodium, aprobarbital, butabarbital, chloral hydrate, chlordiazepoxide, chlordiazepoxide hydrochloride, clorazepate dipotassium, diazepam, diphenhydramine, estazolam, ethchlorvynol, flurazepam hydrochloride, glutethimide, hydroxyzine hydrochloride, hydroxyzine pamoate, lorazepam, methotrimeprazine hydrochloride, midazolam hydrochloride, non prescription, oxazepam, pentobarbital sodium, phenobarbital, phenobarbital sodium, quazepam, secobarbital sodium, temazepam, triazolam, and zolpidern tartrate; and the stimulants dextroamphetamine sulfate, methamphetamine hydrochloride, methylphenidate hydrochloride and, pemoline.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A method for treating a human with a stimulant dependency, said method comprising administering to said human a therapeutically effective amount of pramipexole and a therapeutically effective amount of an antidepressant, wherein said pramipexole is administered intranasally.

2. A method for treating a human with a stimulant dependency, said method comprising administering to said human a therapeutically effective amount of pramipexole and a therapeutically effective amount of an anticonvulsant, wherein said pramipexole is administered intranasally.

3. A method for treating a human with a cocaine craving dependency, said method comprising administering to said human a therapeutically effective amount of pramipexole and a therapeutically effective amount of an antidepressant, wherein said pramipexole is administered intranasally.

4. A method for treating a human with a cocaine craving in a human, said method comprising administering to said human a therapeutically effective amount of pramipexole and a therapeutically effective amount of an anticonvulsant, wherein said pramipexole is administered intranasally.

5. The method of claim 2 or 4, wherein said anticonvulsant is lamotrigine.

6. The method of any one of claims 1–4, wherein said pramipexole is administered at a dose ranging from 1.5 mg/day to 6.0 mg/day.

7. The method of claim 6, wherein said pramipexole is administered at a dose ranging from 1.5 mg/day to 4.5 mg/day.

8. The method of claim 1 or 2, wherein said stimulant dependency involves a stimulant craving.

9. The method of any one of claims 1–4, wherein said pramipexole is administered intranasally.

* * * * *

UNITED STATES PATENT AND TRADEMARK OFFICE
CERTIFICATE OF CORRECTION

PATENT NO. : 6,750,235 B1
DATED : June 15, 2004
INVENTOR(S) : Rosenbaum

It is certified that error appears in the above-identified patent and that said Letters Patent is hereby corrected as shown below:

Column 3
Line 8, replace "bad" with -- had --.

Column 4,
Line 50, replace "chiordiazepoxide" with -- chlordiazepoxide --; and
Line 61, replace "metbsuximide" with -- methsuximide --.

Column 5,
Line 32, replace "zolpidern" with -- zolpidem --.

Column 6,
Line 26, replace "in a human" with -- dependency --; and
Lines 40-41, delete "9. The method of any one of claims 1-4, wherein said pramipexole is administered intranasally.".

Signed and Sealed this

Nineteenth Day of July, 2005

JON W. DUDAS
*Director of the United States Patent and Trademark Office*